United States Patent
Lee et al.

(10) Patent No.: US 7,803,844 B2
(45) Date of Patent: Sep. 28, 2010

(54) COMPOSITION FOR PREVENTING AND/OR TREATING BONE DISEASE, PHYSIOLOGICALLY FUNCTIONAL OR HEALTH FOOD CONTAINING THEREOF, AND PHARMACEUTICAL CONTAINING THEREOF AS ACTIVE INGREDIENTS

(75) Inventors: Kun-Hyung Lee, Kasugai (JP);
Byung-Yoon Cha, Kasugai (JP);
Takayuki Yonezawa, Kasugai (JP);
Shinichi Hasegawa, Kasugai (JP);
Je-Tae Woo, Kasugai (JP); Kazuo Nagai, Kasugai (JP)

(73) Assignee: Erina Co. Inc., Tokyo (JP)

( * ) Notice: Subject to any disclaimer, the term of this patent is extended or adjusted under 35 U.S.C. 154(b) by 810 days.

(21) Appl. No.: 11/708,041

(22) Filed: Feb. 20, 2007

(65) Prior Publication Data
US 2007/0232703 A1      Oct. 4, 2007

Related U.S. Application Data

(63) Continuation of application No. PCT/JP2005/022174, filed on Dec. 2, 2005.

(30) Foreign Application Priority Data
Dec. 3, 2004    (JP) ................... JP2004-351907

(51) Int. Cl.
*A61K 31/05* (2006.01)
(52) U.S. Cl. ..................................... 514/731
(58) Field of Classification Search .......... 514/731
See application file for complete search history.

(56) References Cited

FOREIGN PATENT DOCUMENTS

| | | |
|---|---|---|
| JP | 5-51316 | 3/1993 |
| JP | 8-175945 | 7/1996 |
| JP | 8-175946 | 7/1996 |
| JP | 10-338631 | 12/1998 |
| JP | 11-209276 | 8/1999 |
| JP | 2001-321123 | 11/2001 |
| JP | 2002-199850 | 7/2002 |
| JP | 2003-48844 | 2/2003 |

OTHER PUBLICATIONS

Wo, et al.; "Shoyaku Seibun ni yoru Hakotsu Saibo no Bunka Oyobi Hone Kyushu Kino Sogai;" *Associate Journal of Japanese Society for Medical Use of Functional Foods*; vol. 2; No. 2; Nov. 30, 2004; p. 150 and cover sheet (2 Sheets total.).

*Primary Examiner*—Raymond J Henley, III
(74) *Attorney, Agent, or Firm*—Kratz, Quintos & Hanson, LLP

(57) ABSTRACT

The present invention provides the pharmaceutical compositions, the pharmaceutical preparations thereof as an active ingredient, the health food, the food with health-promoting benefits and the like. The present invention provides the above-mentioned pharmaceutical preparations and the like comprising at least one of the compound shown in the following formula (I), physiologically acceptable salt thereof, or hydrate thereof.

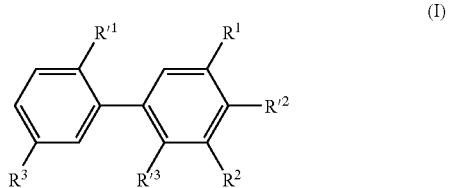

(wherein, $R^{'1}$, $R^{'2}$, and $R^{'3}$ are independently a hydrogen atom, OH, or alkoxy group having C1 to C3, respectively. $R^1$, $R^2$, and $R^3$ are independently a hydrogen atom or alkenyl group having C3 to C5, respectively).

11 Claims, 6 Drawing Sheets

Negative control

Positive control

Honokiol 20μM

Negative control

Positive control

Honokiol 10μM

COMPOSITION FOR PREVENTING AND/OR TREATING BONE DISEASE, PHYSIOLOGICALLY FUNCTIONAL OR HEALTH FOOD CONTAINING THEREOF, AND PHARMACEUTICAL CONTAINING THEREOF AS ACTIVE INGREDIENTS

This application is a continuation of PCT/JP05/22174, filed Dec. 2, 2005 which claims foreign priority to Japanese document JP2004-351907, filed Dec. 3, 2004.

FIELD OF THE INVENTION

The present invention relates to a use of phenylpropanoid dimer compounds as shown in the following formula (I) among those derived from oriental medicine (crude drug). More specifically, it relates to a health food comprising at least one of the phenylpropanoid dimer compounds shown in the following formula (II) or (III), and physiologically available salt thereof or hydrate; a food with health-promoting benefits comprising the same; a pharmaceutical composition having prophylaxis and/or treatment effect of the bone disease; as well as a pharmaceutical agent comprising the pharmaceutical compound as an active ingredient.

[Chemical Formula 1]

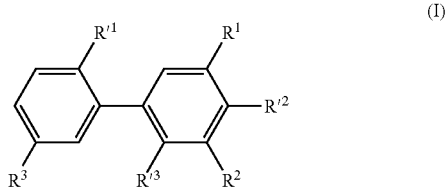

(I)

(wherein, $R'^1$, $R'^2$, and $R'^3$ are respectively hydrogen atom, hydroxyl group, or alkoxy group having $C_1$ to $C_3$; $R^1$, $R^2$, and $R^3$ are respectively hydrogen atom or alkenyl group having $C_3$ to $C_5$.)

[Chemical formula 2]

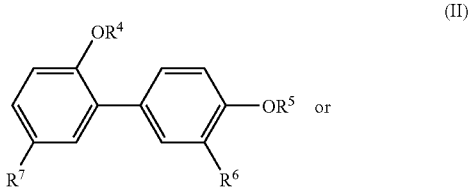

(II)

[Chemical formula 3]

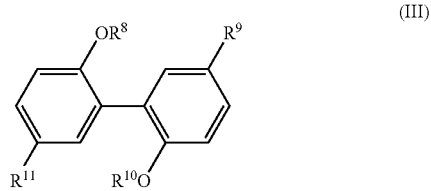

(III)

(wherein, $R^4$, $R^5$, $R^8$ and $R^{10}$ are respectively one substitute selected form the group consisting of hydrogen atom or alkyl group having $C_1$ to $C_3$; alternatively, $R^6$, $R^7$, $R^9$ and $R^{11}$ are respectively alkenyl group having $C_3$ to $C_5$.)

BACKGROUND ART

The bone disease are roughly classified to exogenous disease caused by traumatic bone fracture or stress fracture and so forth; and another disease caused by breakable the bone tissue caused by several disease such as pre-osteoporosis disease, osteoporosis, hypercalcemia, hyperparathormone disease, Paget's disease, arthritis, rheumatism, metastasis of breast cancer, osteomalacia, malignant neoplasm, and nutritional deficiency.

Human bone repeats remodeling and resorption of the bone at every moment. Therefore, when the bone resorption by osteoclastic cells overs the bone remodeling by osteoblast cells, the bone tissue becomes breakable and it causes intrinsic bone disease such as pre-osteoporosis and osteoporosis as described above.

Among these diseases, patients of pre-osteoporosis and osteoporosis are increasing followed by progression for aging of the population. Alternatively, change of diet and reducing the amount of exercise causes decrease in intake of calcium and fixation ratio of it. These accelerate the speed for breaking the osseous tissue.

Bone fracture is defined the situation wherein a part of the osseous tissue is disconnected by being applied external force, and accompanied by significant pain at the fracture site In a normal subject, normally fracture does not occur unless large external force is applied, for example, traffic accident. However, in a person whose bone mass becomes lower and has weakened osseous tissue, the bone fracture sometimes occurs when the external force being not large is applied, for example, he falls down while running or walking. Alternatively, in the person whose bone mass is lowered caused by intrinsic disease such as osteoporosis or pre-osteoporosis, the fracture often occurs by being applied slight external force caused by coughing or fall to a step.

When the fracture is occurred, the following methods for treatment are employed: in general, dislocated bone is corrected the normal position by traction, and if possible, these bones are fixed by using pins or bolts. After that, the fractured site was hold and wait until is repaired spontaneously.

On the other hand, when a patient who has the intrinsic disease such as osteoporosis or pre-osteoporosis, both amounts of calcareous of the bone and bone matrix are decreased, and these causes late spontaneous repairing. When the patient is elder, artus except fractured site becomes too stiff to move while spontaneous repairing, and sometimes the patient become bedridden.

SUMMARY OF THE INVENTION

Problems to be Solved by the Invention

Accordingly, there are strong social needs to shorten the term for repairing fractured bone. Furthermore, pharmaceutical agents used to repairing fracture should have highly effective and safe such as slight side effects.

Conventionally, active vitamin D3, calcitonin and its derivatives, hormone preparations such as estradiol and the like, a variety of calcium preparations have been clinically used.

However, there are problems that these preparations sometimes could not administered p.o., from the view point of the absorption or metabolism; or it was difficult to predict effectiveness in each patient because of individual variability in a receptor level. Therefore, a new preparation for treatment substituting for the conventional preparations is required.

On the other hand, the best way to decrease the patient number is prophylaxis of the bone disease. In general, in order to prevent the disease, the pharmaceutical preparations for prophylaxis are administered to the patient, or a food with health-promoting benefits is taken by the person, depending on the stage how he is close to appear the disease.

Even in the bone disease, there are social needs for effective prophylactic means for preventing the normal subject or patient does not appear the disease from the disease, as well as for treating means for the patients with appearance.

Means for Solving the Problem

Present invention is completed under the above-mentioned situations. That is, inventors of the present invention found that known compounds have new activity to inhibit bone resorption which has been not known at all by now, as a result of screening of the compounds included in plants used as crude drugs from ancient age with bone resorption inhibition, considering their highly safety for patients. Then, they completed the present invention.

As a result of the screening, they clarified that the phenylpropanoid compounds derived from the crude drug have unknown physiological activities. As the examples having such activities, there are mentioned honokiol, magnolol and the like.

Further to these compounds, it is known that they have inhibition activity of OH radical and peroxidation of lipid (see Patent Document No. 1).

Also, it is known that ethanol extract of KOUBOKU (Magnoliae Cortex) has the inhibition activity of acid phosphatase, and honokiol or magnolol has the inhibition activity of the acid phosphatase by itself (see Patent Document No. 2).

Furthermore, diluted-ethanol extract or hot water extract of bark, root bark, trunk material and leaves has the inhibition activity of collagenase (see Patent Document No. 3).

However, there is no report that the above-mentioned phenylpropanoid dimer compounds as mentioned above inhibit the activities of osteoclasts or inhibit bone resorption.

[Patent Document 1] JP H11-209276
[Patent Document 2] JP H10-338631
[Patent Document 3] JP H05-51316

The inventors of the present invention carried out the screening of the compounds inhibiting the bone resorption by the osteoclast under such conditions; they found the highly safe compounds having such effects, derived from natural sources, and completed the present invention.

Namely, the present invention is a composition for prophylaxis and/or treatment of the bone disease comprising at least one of the compounds shown as the following formula (I), physiologically acceptable salt thereof, or hydrate thereof.

[Chemical Formula 4]

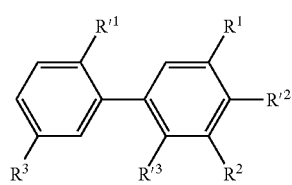

(I)

(wherein, $R'^1$, $R'^2$, and $R'^3$ are respectively hydrogen atom, hydroxyl group, or alkoxy group having C1 to C3. $R^1$, $R^2$, and $R^3$ are respectively hydrogen atom or alkenyl group having C3 to C5.)

Herein, the compounds shown in the above-mentioned formula are preferable those they are those shown as the following formulae (II) or (III).

[Chemical Formula 5]

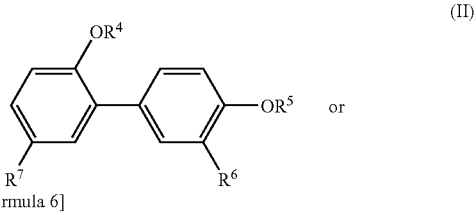

(II)

or

[Chemical Formula 6]

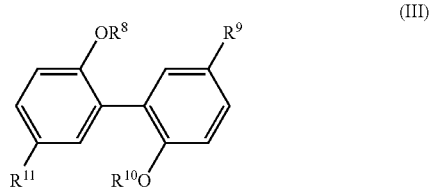

(III)

(wherein $R^4$, $R^5$, $R^8$ and $R^{10}$ is respectively hydrogen atom, or a group selected form the group consisting of alkyl group having C1 to 3. Alternatively, $R^6$, $R^7$, $R^9$ and $R^{11}$ are alkenyl group having C3 to C5.)

Herein, the compounds shown as the above-mentioned formulae (I) to (III) are preferable those shown as the following formulae (IV) or (V)

[Chemical Formula 7]

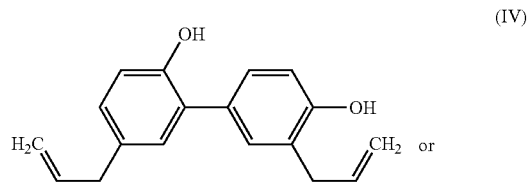

(IV)

or

[Chemical Formula 8]

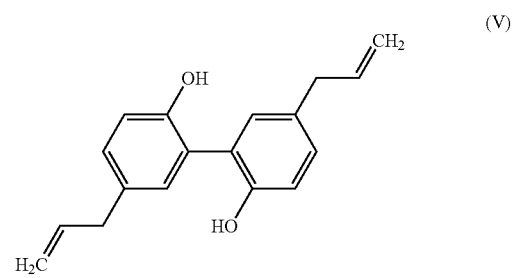

(V)

or physiologically acceptable salt thereof, or physiologically acceptable hydrate thereof.

Furthermore, the composition is produced by mixing at least two compounds as mentioned above, physiologically acceptable salt thereof or hydrate, the composition preferably comprises one of the compounds shown in the above-mentioned formulae (I) to (III), physiologically acceptable salt thereof, or hydrate thereof.

The other aspect of the present invention is a food with health-promoting benefits comprising the above-mentioned compound, physiologically acceptable salt thereof, and hydrate thereof. The other aspect of the present invention is pharmaceutical preparations comprising extracts extracted from a bark of trunks or branches of arbor trees belonged to *Magnolia* genus, which including the compounds shown as the formulae (I) to (V) as mentioned above, physiologically acceptable salt thereof, and physiologically acceptable hydrate thereof.

Herein, arbor trees belonged in the above-mentioned *Magnolia* genus (Magnoliaceae) is preferably selected from the group consisting of *Magnolia officinalis* (Japanese name: Karahou), *Magnolia officinalis* var. *biloba* (Japanese name: Kouboku having leaves concave upward), *Magnolol hypoleuca* (English name: Japanese big-leaf *Magnolia*), *Magnolia macrophylla*, *Magnolia obovata* (English name: Honoki in Japanese name, Japanese big-leaf *Magnolia*), *Magnolia salicifola* (English name: Willow-leaved *Magnolia*), *Magnolia stellata* (English name: Star *Magnolia*), *Magnolia virginiana* (Japanese name: Himetaisanboku, English name: Sweet bay), *Magnolia delavayi*, *Magnolia kobus*, *Magnolia sieboldii* (Japanese name: Oobayamarenge), and *Magnolia wilsonii*, because the above-described compounds are included in them.

Alternatively, among these arbor trees belonged to *Magnolia* genus (Magnoliaceae), the tree selected from the group consisting of *Magnolia officinalis* (Japanese name: Karahou), *Magnolia officinalis* var. *biloba* (Japanese name: Kouboku having leaves concave upward), *Magnolia hypoleuca* (English name: Japanese big-leaf *Magnolia*), *Magnolia obovata* (Japanese name; Honoki, English name: Japanese big-leaf *Magnolia*), *Magnolia salicifola* (English name: Willow-leaved *Magnolia*), *Magnolia stellata* (English name: Star *Magnolia*), *Magnolia virginiana* (Japanese name: Himetaisanboku, English name: Sweet bay), and *Magnolia sieboldii* (Japanese name: Oobayamarenge) is preferably used, because of the contents of the above-mentioned compounds.

Alternatively, the other aspect of the present invention is a pharmaceutical preparation for prophylaxis and/or treatment of bone disease comprising the compositions as an active ingredient for pharmaceutical preparations as described above.

Herein, the amounts of the active ingredient for the pharmaceutical preparation for prophylaxis and/or treatment of bone disease is in a range from 0.1 to 100 mg/preparation is preferable; more preferably from 0.1 to 50 mg, most preferably 0.3 to 10 mg.

As the dosage form of the pharmaceutical preparation for prophylaxis and/or treatment of bone disease, that being administered per os is preferably, and more preferably, they are selected from the group consisting of tablet, powder, capsule, granule, pill, troche, and liquid preparations.

Herein, the pharmaceutical preparation of the present invention may be administered to treat the bone disease described above caused by one reason among the intrinsic disease, exogenous disease, and nutritional deficiency. In the case of the intrinsic bone disease, pre-osteoporosis, the pharmaceutical preparation of the present invention is preferably used to treat the breakable osseous tissue caused by the disease selected from the group consisting of osteoporosis, hypercalcemia, hyperparathormonemia, Paget's disease, arthritis, rheumatism, bone metastasis of breast cancer, osteomalacia, malignant neoplasm, and nutritional deficiency. The pharmaceutical preparation of the present invention is also preferably used to the disease caused by the exogenous reason such as traumatic fracture and stress fracture.

The present invention is also a food with health-promoting benefits comprising the compound selected from the group consisting of the above-mentioned compounds, physiologically acceptable salt thereof, and hydrate thereof.

As additives for the food with health-promoting benefits, the compounds shown as the formulae (I) to (III) as described above, physiologically acceptable salt thereof, and hydrate thereof are preferable. Among them, the compound is more preferably selected from the group consisting of the physiologically acceptable salt thereof and hydrate thereof; and is further preferably selected from the group consisting of sodium salt, potassium salt, ammonium salt, magnesium salt, monohydrate thereof, and dihydrate thereof.

Specifically, the compound is preferably selected from these shown in the following formulae (IV) or (V),

[Chemical Formula 9]

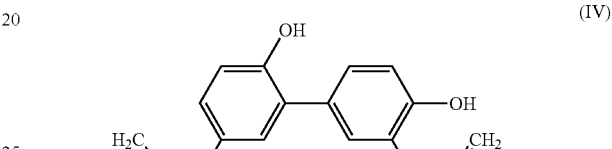

(IV)

[Chemical Formula 10]

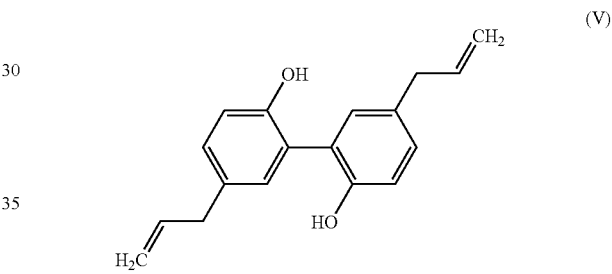

(V)

physiologically acceptable salt thereof, and hydrate thereof; further preferably selected from the group consisting of sodium salt, potassium salt, ammonium salt, magnesium salt, monohydrate thereof, and dihydrate thereof.

Furthermore, it is preferable that the present invention is the food with health-promoting benefits comprises the extracts from the bark of trunks or branches of the arbor trees belonged to *Magnolia* genus, of which extract includes at least one of the compounds shown in the formulae (I) to (V), physiologically acceptable salt thereof, and hydrate thereof. By taking the food with health-promoting benefits including such compounds and the like, the bone diseases may be prevented. Herein, the arbor trees belonged to *Magnolia* genus (Magnoliaceae) is the same as mentioned above.

The food with health-promoting benefit is preferably used to aid the prophylaxis and/or treatment of the bone disease. Herein, the amounts of it selected from the group consisting of the above-mentioned compounds, physiologically acceptable salt thereof, and hydrate thereof included in the food is preferably in the range from 0.1 to 5 mg per 100 g, more preferable in the range from 0.1 to 3 mg. When the amount is in the range from 0.1 to 3 mg, the bone disease is most effectively prevented and/or treated.

Furthermore, the present invention is health food comprising the composition that includes the compound selected from the group consisting of the compounds shown in the formulae (I) to (V) as described above, physiologically acceptable salt thereof, and hydrate thereof. The physiologically acceptable salt thereof and hydrate thereof are the same as described above.

Further, the health food of the present invention preferably comprises the extracts from the bark of trunks or branches of the arbor trees belonged to *Magnolia* genus, of which extract includes at least one of the compounds shown in the formulae (I) to (V), physiologically acceptable salt thereof, and hydrate thereof. By taking such health food including such compounds and the like, the bone diseases may be prevented. Herein, the arbor trees belonged to *Magnolia* genus (Magnoliaceae) is the same as mentioned above.

The health food is preferably used to aid the prophylaxis and/or treatment of the bone disease. Herein, the amounts included in the food of the compounds selected from the group consisting of the above-mentioned compounds, physiologically acceptable salt thereof, and hydrate thereof is preferably in the range from 0.1 to 5 mg per 100 g, more preferable in the range from 0.1 to 3 mg. When the amount is in the range from 0.1 to 3 mg, the bone disease is most effectively prevented and/or treated.

Effect of the Invention

According to the present invention, the food with health-promoting benefits, health food, pharmaceutical composition for prophylaxis and/or treatment of the bone disease, and pharmaceutical preparations for bone disease, which have excellent inhibition effects for both osteoclast formation and bone resorption are provided.

BEST MODE FOR CARRYING OUT THE INVENTION

Figure 1A:
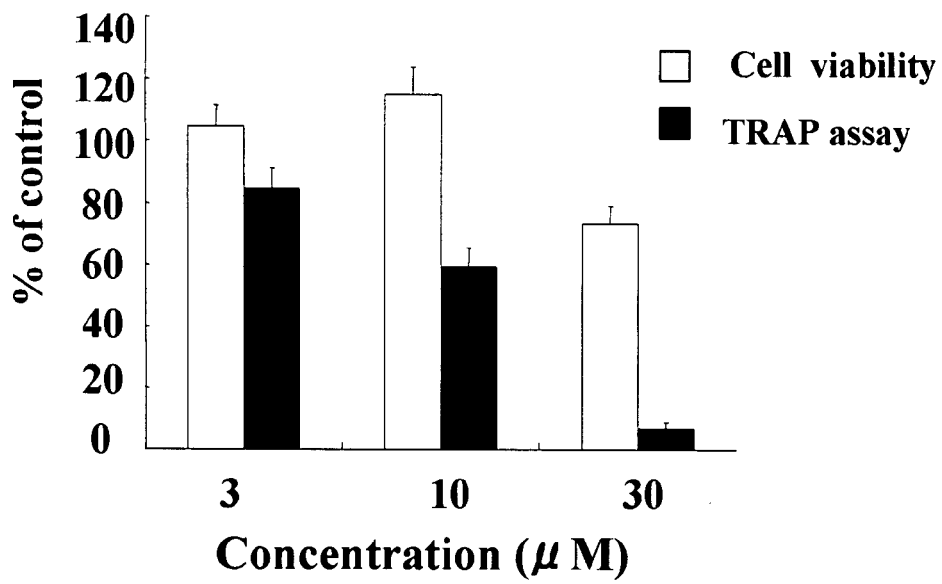
FIG. 1A shows the dose dependent differentiation inhibiting effect of honokiol to MφRAW264 cell line, which is stimulated by 50 ng/mL of osteoclast diffentiation factor (ODF/RANKL)

The present invention is explained in detail herein below. The compound, physiologically acceptable salt thereof, and hydrate thereof included in the pharmaceutical composition for the prophylaxis and/or treatment of the present invention is called as phenylpropanoid dimer; and it is shown as the following formula (I).

[Chemical Formula 11]

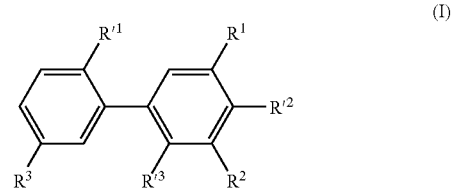

(I)

(wherein $R'^1$, $R'^2$, and $R'^3$ are independently hydrogen atom, hydroxyl group, or alkoxy group having C1 to C3, respectively. $R^1$, $R^2$, and $R^3$ are independently hydrogen atom or alkenyl group having C3 to C5.)

More specifically, they are shown as the following formulae (II) or (III).

[Chemical Formula 12]

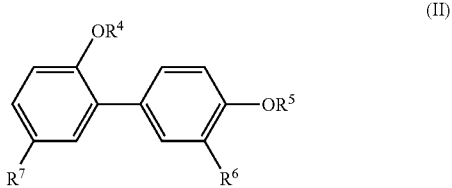

(II)

[Chemical Formula 13]

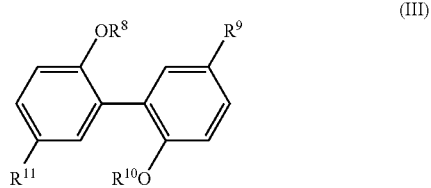

(III)

(wherein $R^4$, $R^5$, $R^8$ and $R^{10}$ are respectively a substitute selected from the group consisting of hydrogen atom and alkyl group having C1 to C3. Furthermore, $R^6$, $R^7$, $R^9$ and $R^{11}$ are alkenyl group having C3 to C5.)

Phenylpropanoid is a general name of a phenyl compound having alkenyl group, and a compound coupled between β carbons of two phenylpropanoid molecules is defined as phenylpropanoid dimer.

The term "lignan" means phenylpropanoid dimer in the narrow meaning. However, in this specification, it also includes neolignan, sesquilignan and dilignan.

As described above, lignan is composed of a class of compounds having phenyl backbone and alkenyl group or hydroxyl group and so forth and those including alkoxy derivatives. Lignan is widely distributed to higher plant, particularly contained in xylem.

As the compounds shown in the above-mentioned formulae (I) or (II), for example, honokiol shown in the following formula (IV),

[Chemical Formula 14]

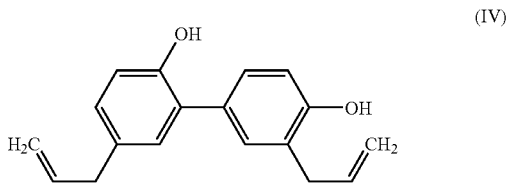

(IV)

and magnolol shown in the following formula (V) are mentioned.

[Chemical Formula 15]

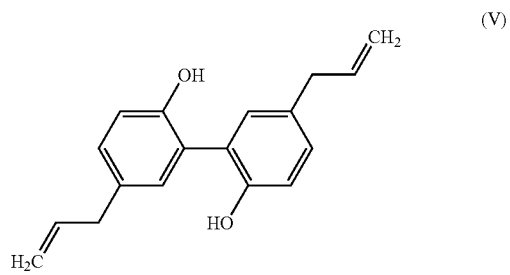

(V)

Wherein, honokiol is the phenylpropanoid dimmer compounds contained in the bark of the trunk and branches of Honoki tree belonged to Magnolia (*Magnolia*) Magnolol is also phenylpropanoid dimmer compound, but it is contained in *Magnolia officinalis, Magnolia officinalis* var. *biloba, Magnolia obovata*, and so forth.

As the physiologically acceptable salt thereof, for example, there are mentioned such as sodium salt, potassium salt, and ammonium salt. As hydrate compounds, there are mentioned, for example, monohydrate, dehydrate, and so forth.

Phenylpropanoid dimmer compound as mentioned above may be used solely for producing the composition for the pharmaceutical preparations of the present invention, and may be used more than two kinds in combination depending on the needs. Alternatively, crude drugs comprising these compounds or physiologically acceptable salt thereof, hydrate thereof may be used solely or more than two kinds in combination.

There are crude drugs, for example, such as KARAKOUBOKU and WAKOUBOKU obtained from *Magnolia officinalis, Magnolia officinalis* var. *biloba, Magnolia hypoleuca, Magnolia obovata* generated in China or Japan.

Phenylpropanoid dimer such as honokiol shown in the formula (IV) and magnolol shown in the formula (V) as mentioned above may be synthesized by using known methods or according to such methods. These compounds may be purchased from commercially available ones.

Alternatively, above-mentioned phenylpropanoid dimer compounds may be obtained by extraction from plants as natural resources and then isolated. For example, a method for isolating honokiol from plants as raw materials is described in below.

The bark of the trunk or branches of magnolol obotava belonged to magnolol is shredded and placed in a container. Then, hydrous methanol or hydrous ethanol is added to the container to obtain either extracts. Obtained extract is dissolved in water, and then is degreased by using low polar solvent such as petroleum ether and benzene. Then, butanol is added and honokiol and its derivatives are extracted in butanol phase. Herein, honokiol and its derivative contain honokiol, its physiologically acceptable salt, and its hydrate.

Honokiol and its derivatives thus extracted may be used as crude extracts, but may be purified to obtained purified sample as appropriate. The purification may be performed by using conventional procedure. For example, honokiol and its derivatives are respectively eluted by using a step gradient column chromatography, wherein silica gel is used as a solid phase, and chloroform/methanol is used as mobile phase; methanol ratio in the mobile phase is sequentially increased. Subsequently, the eluate is purified to obtain as a white powder and so forth.

The compound including magnolol, physiologically acceptable salt thereof, and hydrate thereof as shown in the above-mentioned formulae (I) to (III) are simultaneously eluted and purified.

The pharmaceutical compositions are produced by using the compound, physiologically acceptable salt thereof, and hydrate thereof as shown in the above-mentioned formulae (I) to (III) as described below.

When honokiol is used solely to prepare the pharmaceutical composition, crystalline obtained described above is treated according to the conventional procedure, and then mixed with excipient and the like.

Alternatively, when honokiol and magnolol are used in combination, they are mixed at the desired ratio of honokiol 1 to magnolol 0.1 to 10. Then, the mixture is subjected to prepare the pharmaceutical composition similarly to the case wherein honokiol is used solely.

As the pharmaceutical preparations including such pharmaceutical compositions, there are mentioned parenteral preparations such as injectables, suppositories, aerosols, percutaneous, and the like; and oral administrations such as tablets, powders, capsules, pills, troches, liquids and the like. Herein, above-mentioned tablets include sugarcoated tablets, a coating tablets, and buccal preparations; the capsules include both of hard gelatin capsules, soft elastic capsules. The granules also include coated granules. The above-mentioned liquid preparations include suspensions, emulsions, syrups, elixirs, and so forth, and the syrup includes dry syrup.

Note that the respective preparations include sustained release preparations and non-sustained release preparations.

These preparations may be produced according to the preparation method of pharmaceuticals, using physiologically acceptable carriers, excipients, disintegrators, lubricants, colorants, and the like described on Japanese Pharmacopoeia.

As the carriers or excipient, there are mentioned for example, lactose, glucose, sucrose, mannitol, potato starch, corn starch, calcium carbonate, calcium phosphate, calcium sulfate, crystalline cellulose, glycyrrhiza, gentian powder, and the like.

As a binder, there are mentioned, for example, starch, traganth gum, gelatin, syrup, polyvinylalcoho, polyvinylether, polyvinylpyrrolidone, hydroxypropylcellulose, methylcellulose, ethylcellulose, carboxymethylcellulose, and the like.

As the lubricant, there are mentioned, for example, starch, agar, gelatin powder, sodium carboxymethylcellulose, calcium carboxymethylcellulose, crystalline cellulose, calcium carbonate, sodium bicarbonate, sodium alginate, magnesium stearate, talc, hydrogenated vegetable oil, macrogol and the like.

Any colorant acceptable to add the pharmaceuticals may be used without any limitation. Except these additives, corrigents and so forth may be used as appropriate.

When the tablet or granule is produced, they may be coated by using sucrose, gelatin, hydroxypropylcellulose, purified shellac, glycerin, sorbitol, ethylcellulose, hydroxypropylcellulose, hydroxypropylmethylcellulose, polyvinylpyrrolidone, cellulose acetate phthalate, hydroxypropylmethylcellulose phthalate, methyl-methacrylate, methacrylate polymers, and the like; or coated by multiple layers formed by them.

Furthermore, capsule preparations may be produced by filling a capsule made of, for example, gelatin or ethylcellulose with the granule or powder.

When the injectable is produced by using the above-mentioned compounds, physiologically acceptable salt thereof, or hydrate thereof, pH adjuster, buffering agent, stabilizer, solubilizing agent and so forth may be added as appropriate.

When the prophylaxis and/or treatment preparation for bone disease as described above is administered to patients, the dosage is varied depending on their thickness of the disease, age, weight, physical condition and the like. In general, the preparation is preferably administered at single dosage or plural dosage per day at the dose range between 1 mg to 2,000 mg/kg, more preferably 1 mg to 1,000 mg/kg, in parenteral or per os. The dose and administration numbers may be changed depending on the above-mentioned conditions as appropriate.

When the pharmaceutical composition that contains honokiol solely or in combination with other phenylpropanoid, for example, magnolol as active ingredients, is included in the pharmaceutical preparations, the amount in the preparation is preferably in the range from 0.1 to 100 mg, more preferably in the range from 0.1 to 50 mg, most preferably in the range from 0.3 to 10 mg.

When the amount of the honokiol or other phenylpropanoid is less than the lower limit described above, the bone resorption effect is insufficient; in contrast, when they are over the upper limit, the bone resorption effect is not correspond to the amount included. Furthermore, the amount over the upper limit sometimes shows cytotoxicity to cause undesirable side effect for a human body.

The food with health-promoting benefits or health food having the prophylaxis and/or treatment effect for the bone disease may be provided by adding the above-mentioned composition of the present invention as appropriate.

In the specification, the "food with health-promoting benefit" is defined as the food comprising components, which enables to give benefits superior than its original ones.

Alternatively, the "health food" is defined as powders, granules, tablets or capsules of which main ingredients are crude or purified products including components useful for maintenance and improvement of health; it also includes diet supplement to aid to intake nutrient compositions short on a daily basis.

The composition of the present invention may be added, for example, bread, cookies, biscuit, barley or coarse cereal as an additive for rice diet, noodles such as Japanese wheat noodle, buckwheat noodle, and pasta; dairy product such as cheese and yogurt; jam, mayonnaise; processed soy product such as soybean paste and soy source; non-alcoholic beverage such as tea, coffee, cocoa, carbonated drinks, and non-alcoholic fruit juice beverages; alcoholic beverages such as medical alcoholic beverages and the like; snacks such as candy and chocolate; chewing gum; rice crackers; and confectioneries made of beans such as bars of sweet jellied bean paste; to provide the food with health-promoting benefits.

Note that when the composition is added to above-mentioned yogurt, soy source, or other beverages, auxiliaries or stabilizing agents may be also added to them to inhibit to form crystals and precipitation of the present invention.

Furthermore, the health food may be provided by mixing the compositions of the present invention solely or in combination according to the conventional procedure for preparing the powder, granule, tablet or capsule.

Herein, in order to obtain the composition of the present invention as the powder, the extract obtained during is condensed, and then dried by using methods such as freeze drying, spray drying, or vacuum drying. After that, the dried sample may be ground by using a sample mill, blender, mixer and the like. Alternatively, corn starch, potato starch, dextrin, cyclodextrin, flour of oystershell and so forth may be added as appropriate.

The tablet may be prepared by compressing the powder to which the binder is desirably added. After that, the obtained tablet may be coated by using sucrose or gelatin to prepare the sugarcoated tablet, or coated by other coatings to prepare an enteric coated tablet.

Furthermore, the granular powder is prepared by using the powder obtained as described above according to the conventional procedure; thereby the granule may be prepared. By filling capsules with the above-mentioned powder or granule powder, the capsule may be prepared.

EXAMPLES

The present invention is explained more detail by using Examples, however the present invention is not limited to the examples in below.

Example 1

(1-1) Inhibition Assay of the Early Phase Differentiation of Osteoclast

Macrophage RAW264 cell line (RIKEN. cell No. CB0535, herein below, referred to as "MφRAW264"), which may differentiate to osteoclast-like cells, was used in the inhibition assay of the early phase differentiation of osteoclast. α-MEM (Invitrogen Co., Cat. No. 11900-024) including 10% of fetal bovine serum (Asahi Technoglass Co., (IWAKI), Cat. No. IWK-500) was used for cultivating MφRAW264. Osteoclast differentiation factor (ODF/RANKL) was purchased from Pepro Tech Inc., Cat. No. 310-01.

Honokiol is purchased from Wako Pure Chemical Inc., Cat. No. 089-04951. 96 well Microplate and 100 mm φ dish were purchased from Invitrogen Co., Cat. No. 161093 and 172958, respectively. Magnolol was purchased from Wako Pure Chemical Industries Ltd., Cat. No. 137-09081.

Ethanol, acetone, formaldehyde and sodium chloride were purchased from Wako Pure Chemical Industries Ltd.

(1-2) Inhibition Assay I of the Early Phase Differentiation of Osteoclast

Inhibition assay I of the early phase differentiation of osteoclast was performed for evaluating the inhibition level of the bone resorption in vitro, the differentiation assay of osteoclast from MφRAW264 cells in early stage. Results of the osteoclast assay were evaluated by determining tartrate resistant acid phosphatase (TRAP) activity, an early stage differentiation marker, and TRAP staining. By using these two indices, activities of flavones from MφRAW264 cells to osteoclast are quantitatively evaluated.

MφRAW264 cells were suspended in a α-MEM supplemented 10% of fetal bovine serum (FBS), which is referred to as "10% FBS-MEM herein below", and plated at $1\times10^5$ cells/10 mL in 100 mm φ dishes. Then, the dishes were incubated under the presence of 5% of $CO_2$, at 37° C. for 3 days. After confirmed that the plated cells in the dishes became confluent, the incubation was finished. Subsequently, when the cells became confluent, they were treated by using 0.05% of trypsin and Hank's balanced salt solution containing 0.53 mM of EDTA (0.05% Trypsin-0.53 mM EDTA/HBSS (Invitrogen Co., Cat. No. 25300-054) to scrape them, and then suspended in 10% FBS-MEM to plate $0.4\times10^4$ cells/0.1 mL per each well of 96-well microplates. Then, the plates were incubated one day under the same condition as described above.

Osteoclast differentiation factor (ODF/RANKL) was dissolved in 10% FBS-MEM to prepare 100 ng/mL of solution. Alternatively, a stock solution of honokiol was prepared at the concentration of 10 mM in methanol, and stored at −20° C. When honokiol treatment was performed, the stock solution was diluted to prepare the solutions having 100 times higher concentration against the treatment concentration (3 mM, 1 mM, 300 μM), and added to each well at the final concentration of the solvent lower than 1% (2 μL/well). Equal volume of methanol was solely added into the control wells. Honokiol used in the following experiments were the solutions having each concentration prepared as described above.

To 96 wells, 0.1 mL of ODF/RANK was added at the final concentration of RANKL, 50 ng/mL, and honokiol solutions were added to them (final concentration of honokiol was 3 μM, 10 μM and 30 μM respectively). Equal volume of methanol without honokiol was added into the control wells.

The plates were incubated under the presence of 5% $CO_2$, at 37° C. for 3 days, and then the activity of tartrate resistant acid phosphatase was measured as follows.

Incubation medium in each well of the 96-well microplate was discarded. Then plate was washed by using phosphate buffered saline (PBS). Subsequently, the wells were filled with PBS including 10% of formaldehyde (hereinafter, it referred to as "10% HCHO—PBS") to fix the cells. Furthermore, the fixation was performed by using ethanol-acetone mixture (1:1) for 1 minute. After the fixation, the fix mixture was discarded from the wells; and dried at room temperature. After drying, tartrate resistant acid phosphatase activity was determined (hereinafter, it is referred to as "TRAP assay"), and staining of cells in the well was performed.

The determination of TRAP activity in the incubated cells were performed by adding 0.1 mL of 3.7 mM p-nitrophenoldisodium hydrogenphosphate and 50 mM citrate buffer (pH 4.6) including 10 mM tartrate to all wells, and reacted at 37° C. for 30 minutes. Thirty minutes later, the reaction was terminated by adding 0.1 mL of 0.1 M NaOH, and released p-nitrophenol was determined by the spectrophotometer (Dainippon Pharmaceutical Co. Ltd.) at wave length 405 nm.

The result of the early stage differentiation inhibition assay of osteoclast was shown as control % when TRAP activity of the control group was 100.

Furthermore, conditions of the tartrate resistant acid phosphatase in the cells were confirmed by using TRAP staining. For TRAP staining, the solution including 5 mg of Naphtol AS-MX phosphate (SIGMA Co., Cat. No.: N-4875) dissolved in 0.5 mL of N,N-dimethylformamide as a substrate, and 30 mg of Fast red violet LB salt (SIGMA Co., Cat. No. F-1625) dissolved in 50 mL of 50 mM sodium tartarate/0.1 M sodium citrate buffer (pH 5.0) as a pigment were prepared and used. Namely, as the same as TRAP assay, the medium was removed after incubation. Then, the layer of cell was washed by PBS, and then fixed by 10% HCHO—PBS at room temperature in 15 minutes. Next, the further fixation was performed by using ethanol-acetone solution (1:1) for 1 minute. Subsequently, the fixed solution was discarded and dried at room temperature. Subsequently, TRAP staining solution was added, and stained for 20 to 30 minutes. After staining, the staining solution is discarded and washed under running water and dried; then, the plates were observed under a microscope. Results were shown in FIG. 1A. In FIG. 1, ratios of TRAP activity in the cells, which were obtained in the osteoclast early stage differentiation inhibition assay, were shown as solid columns (see FIG. 1).

As shown in FIG. IA, TRAP activity was dose-dependently inhibited when honokiol was added. The results demonstrated that honokiol inhibited the osteoclast formation from MφRAW264 cells.

(1-3) Inhibition Assay I of the Early Phase Differentiation of Osteoclast

In the above-mentioned (1-2), the same inhibition assay I was performed instead of honokiol to magnolol and their concentration used was at the range from 20 to 60 μM. The results were shown in FIG. 1B.

Figure 1B:
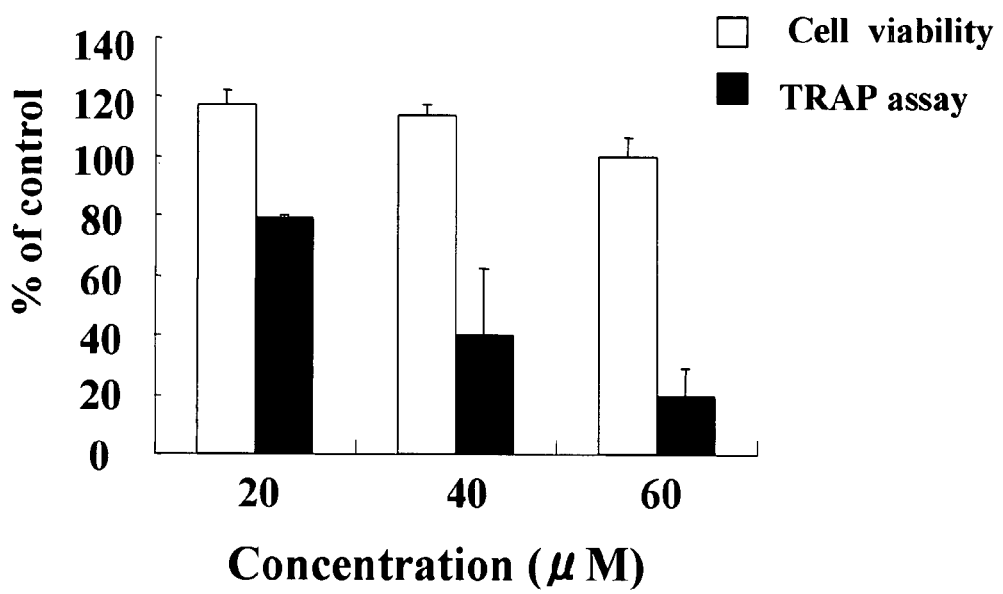
FIG. 1B shows the dose dependent differentiation inhibiting effect of Magnolol to MφRAW264 cell line, which is stimulated by 50 ng/mL of osteoclast diffentiation factor (ODF/RANKL)

As clearly shown in FIG. 1B, TRAP activity was dose-dependently inhibited, when magnolol was added. The results demonstrated that magnolol inhibited the osteoclast formation from MφRAW264 cells.

Example 2

Proliferated Cell Number Counting Assay (2-1) Materials and the Like

The cell line, media, serum, 96-well microplate, 100 mm φ dish, honokiol, and other reagent were the same as these used in Example 1. 10% FBS-MEM solution including osteoclast differentiation factor (ODF/RANKL), and methanol solution of honokiol were prepared similarly to those in Example 1.

(2-2) Inhibition Assay I of the Early Phase Differentiation of Osteoclast

As a non-RI method for determining cell proliferation and cell viability, color reaction by using XTT was employed. MφRAW264 cells were suspended in 10% FBS-MEM, and plated into the 96-well microplate at $0.4\times10^4$ cells/0.1 mL; then incubated for 1 day. Subsequently, 10% FBS-MEM solution of osteoclast differentiation factor (ODF/RANKL), 100 ng/mL, was added into 0.1 mL per well at final concentration of RANKL, 50 ng/mL. At the same time, honokiol solution at respective concentration was added into the wells. For the control wells, equal volume of methanol not including honokiol was added.

After 3 days incubation, the proliferated cells were counted by using commercially available Cell Proliferation Kit II (Roche Diagnostics Inc., Cat. No. 1 465 015) to obtain the cell viability. The procedure was carried out according to the instruction manual attached, and brief summaries were as follows.

XTT labeling reagent and electron coupling reagent included in the kit were mixed at the ratio of 50:1, and 50 μL of mixture was added per 0.1 mL of medium in each well;

then reacted for 4 hours at 37° C. After the termination of the reaction, absorbance at 492 nm of the wave length was measured by using ELISA plate reader (Dainippon Pharma Co.), wherein the reference wave length was 690 nm.

Results were shown as the ratio of cell viability of honokiol treated wells against the control wells, when that of the control wells is 100(%). Results were shown in FIG. 1A. In FIG. 1A, the cell viability obtained from the cell proliferation assay was shown as white columns.

As clearly shown in FIG. 1, the cell viability was decreased to 70% at the lowest, when the concentration of honokiol increased to 10 times higher. The results demonstrated that honokiol does not show non-specific cytotoxicity to MφRAW264 cells; and the proliferation from MφRAW264 cells to osteoclast by RANKL was dominantly inhibited by honokiol, depending to the concentration ($IC_{50}$=15 μM).

(2-3) Cell proliferation Counting Assay II

In the above-mentioned (2-2), the same cell proliferation counting assay II was performed instead of honokiol to magnolol and their concentration used was at the range from 20 to 60 μM. The results were shown in FIG. 1B.

As clearly shown in FIG. 1B, the cell viability was seldom decreased, when the concentration of magnolol was 3 times higher.

The results demonstrated that magnolol does not show non-specific cytotoxicity to MφRAW264 cells; and the proliferation from MφRAW264 cells to osteoclast by RANKL was dominantly inhibited by magnolol, depending on the concentration of it ($IC_{50}$=30 μM).

Example 3

Inhibition Assay of the Early Stage Cell Differentiation of Osteoclast II (3-1) Materials and the Like In the example 3, M-CSF dependent cells derived from mice bone marrow cells (BMM) were used instead of MφRAW264 cells used in the examples 1 and 2, in order to evaluate the bone resorption in vitro. Mouse bone marrow cells were obtained from femurs and shanks of male ddy mice from 6 to 9 week age (Chubu Kagaku Shizai Co. Ltd.)

Except streptomycin sulfate, sodium penicillin G (Invitrogen Co., Cat. No. 15140-122), Tumor growth factor β (TGF-β, SIGMA INC., Cat. No. T-7039), and Macrophage colony stimulation factor (M-CSF, PEPRO TECH INC., Cat. No. 300-25), the same materials and so forth were used as those used in the example 1. By using TRAP Activity determined and TRAP staining as indices similarly to these in the example 1, activities by honokiol and magnolol against osteoclast differentiation were evaluated.

(3-2) Inhibition Assay of the Early Stage Differentiation of Osteoclast II

From 6 to 9 week ages of ddy mice, the femurs and shanks were excised. The bone row cells were extruded from these bones by using a syringe with 22 G×1 and ¼ gauge needle to obtain.

Obtained bone marrow cells were suspended in 10% FBS-MEM supplemented with 100 μg/mL of sodium streptomycin, 100 U/mL of sodium penicillin G, 50 ng/mL of M-CSF, and 1 ng/mL of TGF-β, and then inoculated to each well of the 96-well microplate at the cell concentration of 1×10⁶ cells/0.1 mL/well. Then, the plates were incubated under the presence of 5% $CO_2$, at 37° C.

After 3 days incubation, the culture medium was exchanged to that including 50 ng/mL of M-CSF and 50 ng/mL of osteoclast differentiation factor (DF/RANKL), simultaneously honokiol prepared as the same concentration as used in the example 1 was added. The medium of the control group was exchanged that including M-CSF and ODF/RANKL, but no honokiol. The plates were further incubated under the condition of the presence of 5% $CO_2$, at 37° C.

After 1.5 days from the medium exchange, tartrate resistant acid phosphatase activity, the early stage differentiation marker, was measured. Medium in each well was discarded and washed plate with PBS, the cells in the well was fixed for 15 minutes by using 10% HCHO/PBS. Furthermore, the cells were fixed by using ethanol-acetone (1:1) mixture. After fixation, the fixed mixture was discarded and dried at room temperature. After drying, tartrate resistant acid phosphatase (TRAP) of the cells in each well was measured and stained similarly to those in the example 1. Results were shown in FIG. 2A.

In FIG. 2, the assay result of the TRAP activity in the bone marrow cells cultured in the medium supplemented with honokiol was shown as solid columns.

Figure 2A:
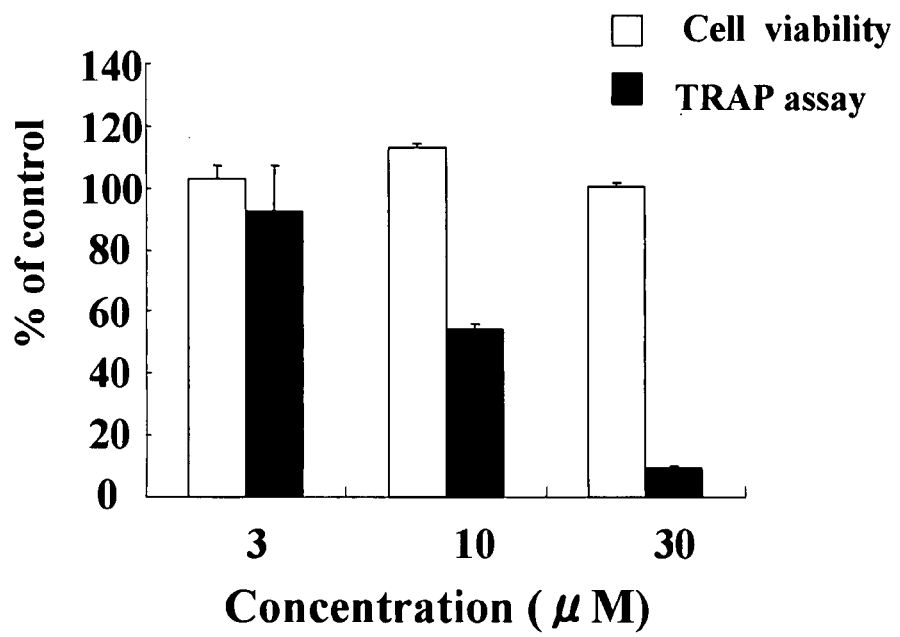
FIG. 2A shows the dose dependent differentiation inhibiting effect of honokiol to M-CSF dependent cell derived from mouse bone marrow cells, which is stimulated by 50 ng/mL of osteoclast diffentiation factor (ODF/RANKL)

Alternatively, the cell proliferation counting assay was performed as the same as that in the example 1, the cell viability was obtained. The result was shown in FIG. 2A. In FIG. 2A, the cell viability was shown as white columns. The assay result of TRAP activity and the cell proliferation counting were shown at the ratios (%) when these of the control wells were 100.

As clearly shown in FIG. 2A, TRAP activity was inhibited, depending on the dose of honokiol added. This means that the osteoclast formation was inhibited by honokiol in dose dependent manner.

Furthermore, from the result of XTT assay (the cell proliferation number counting assay), it was demonstrated that honokiol did not show non-specific cytotoxicity to them. Accordingly, it was demonstrated that honokiol did not show the non-specific cytotoxicity, but the differentiation from the M-CSF dependent cells derived from the mice bone marrow cells to osteoclast induced by RANKL was significantly inhibited in the dose dependent manner ($IC_{50}$=10 μM).

(3-3) Inhibition Assay of the Early Stage Differentiation of Osteoclast II

The inhibition assay of the early stage differentiation of osteoclast was carried out similarly to the described above, except honokiol used in the above mentioned (3-2) was substituted to magnolol, and its concentration was from 20 to 60 μM.

Figure 2B:
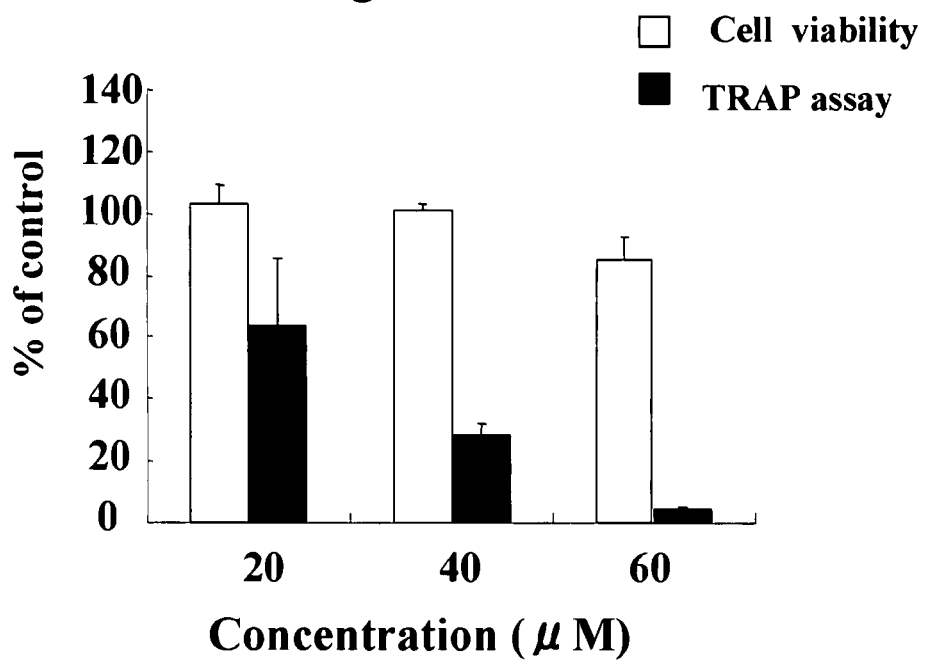
FIG. 2B shows the dose dependent differentiation inhibiting effect of magnolol to M-CSF dependent cell derived from mouse bone marrow cells, which is stimulated by 50 ng/mL of osteoclast diffentiation factor (ODF/RANKL)

The result was shown in FIG. 2B. TRAP activity was dose-dependently inhibited by adding magnolol. From the result, it was demonstrated that magnolol did not show the non-specific cytotoxicity, but the differentiation from the M-CSF dependent cells derived from the mice bone marrow cells to osteoclast induced by RANKL was significantly inhibited in the dose dependent manner ($IC_{50}$=30 μM).

Example 4

Actin Ring, Osteoclast Activating Structure, Formation Assay I (4-1) Materials and the Like MφRAW264 cells, fetal bovine serum, α-MEM, ODF/RANKL, 96-well microplate, and honokiol were the same as those used in the example 1, and prepared similarly to use. PD98059 was purchased from CALBIOCHEM Inc., Cat. No. 153000.

(4-2) Actin Ring Formation Assay I

MφRAW264 cells were suspended in 10% FBS-MEM, and plated at the concentration of $0.8 \times 10^5$ cells/0.1 mL/well into each well of the 96-well microplate; then cultured under the condition in the presence of 5% $CO_2$, 37° C. for one day. After that, 0.1 mL of the medium including 100 ng/mL of ODF/RANKL and 20 µM PD98059 was added, and further incubated under the same condition (final concentration of RANKL was 50 ng/mL, and that of PD98059 10 µM).

In order to promote the differentiation to the activated osteoclast, two days after the addition of ODF/RANKL and PD98059, the medium was exchanged to that including 50 ng/mL of ODF/RANKL as described above; then the plate was incubated until the actin ring, the activated structure of osteoclast, formation was confirmed. After actin ring was formed, honokiol prepared as the same as that prepared in the example 1 was added, and cultured further one day. For the control wells, equal volume of methanol not including honokiol was added, and cultured for one more day.

One day after when honokiol was added to culture, TRAP staining of the tartrate resistant acid phosphatase (TRAP) in each well, similarly o those performed. Results were shown in FIG. 3.

Figure 3A:
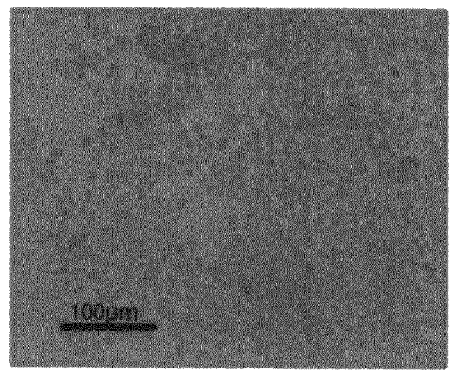
FIG. 3A is a photograph that shows the inhibition effect to hold actin ring formed by MφRAW264 cell line by honokiol (a negative control)
Figure 3B:
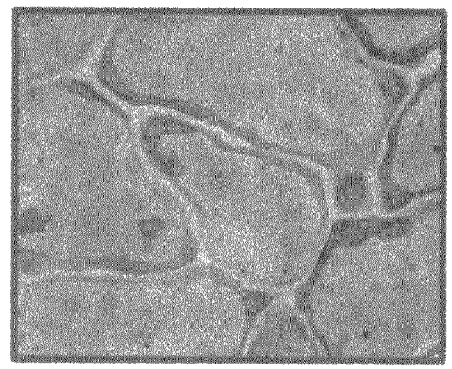
FIG. 3B is a photograph that shows the inhibition effect to hold actin ring formed by MφRAW264 cell line by honokiol (a positive control)
Figure 3C:
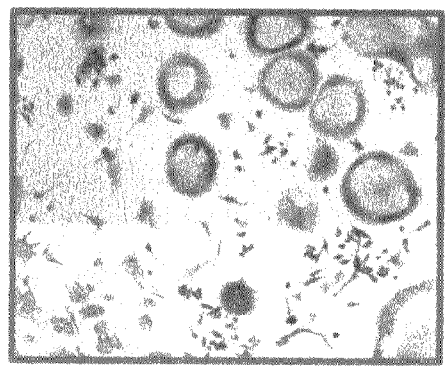
FIG. 3C is a photograph that shows the inhibition effect to hold actin ring formed by MφRAW264 cell line by honokiol.

As shown in FIG. 3, actin ring formation was observed in the control wells (see FIGS. 3A and 3B); however, the actin rings were destructed in honokiol treatment wells, when 20 µM honokiol was added (see FIG. 3C).

The actin rings were activated structure of osteoclast, which was formed by the culture of the MφRAW264 cells treated with both ODF/RANKL and PD98059. Therefore, honokiol inhibited not only the differentiation of osteoclast but also maintenance of the activated structures, thereby inhibiting the bone resorption.

Example 5

Pit Formation Assay of Mature osteoclast (5-1) Materials and the Like

Except streptomycin sulfate and sodium penicillin G, TGF-β, and M-CSF, the same materials used in the example 1 were employed. Streptomycin sulfate and sodium penicillin G, TGF-β, and M-CSF were used as the same ones used in the example 3.

5-2) Pit Formation Assay

Alternatively, the bone marrow cells were obtained form the shanks and femurs from ddy mice of 6 to 9 week age, similarly to the methods employed in the example 3.

Obtained bone marrow cells were suspended in 10% FBS-MEM including 100 U/mL of sodium penicillin G, 100 µg/mL of streptomycin sulfate, 50 ng/mL of M-CSF, and 1 ng/mL of TGF-β. Then, the suspension was plated at $0.85 \times 10^6$ cells/0.1 mL/well into the 16 well multi slide plate (Bio-Coat Osteologic Bone Cell Culture System; BD Biosciences, Cat. No.: 354609) which was coated by calcium phosphate apatite, and incubated under the presence of 5% $CO_2$, at 37° C.

After three days incubation, the medium was exchanged to that including 50 ng/mL of M-CSF and 100 ng/mL of osteoclast differentiation factor (ODF/RANKL). Subsequently, the plates were incubated under the same condition until the formation of actin ring, the osteoclast activated structure, was confirmed. After the actin ring was formed, honokiol prepared as the same concentration used in the example 1 is added, and incubated further one day. To the control group, the solvent without honokiol was added.

After 1 day incubation from the addition of honokiol, the medium in the well was discarded, and the plate was washed by using phosphate buffered saline (PBS); then, 0.1 mL of 0.1 M NaOH is added to every well to dissolve the cells in it. When the dissolution of the cells was finished, NaOH solution was discarded, and the plate was washed by using running water. Subsequently, the plate was dried at room temperature, and observed by using a microscope. Results were shown in FIG. 4.

Figure 4A:
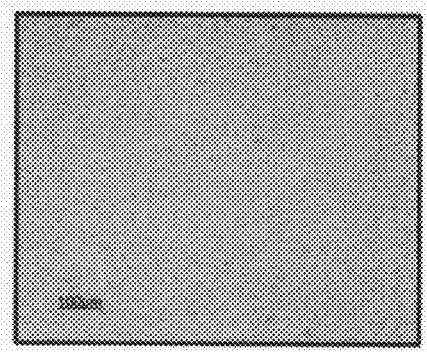
FIG. 4A is a photograph that shows the inhibition effect to pit formation from M-CSF dependent cell from mouse bone marrow cell by honokiol (a negative control)
Figure 4B:
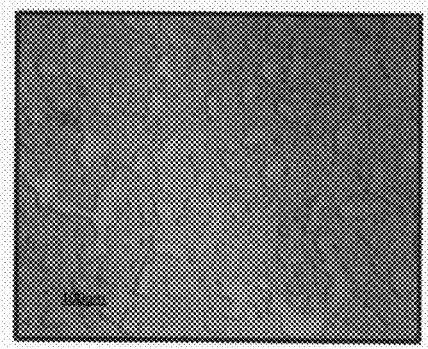
FIG. 4B is a photograph that shows the inhibition effect to pit formation from M-CSF dependent cell from mouse bone marrow cell by honokiol (a positive control)
Figure 4C:
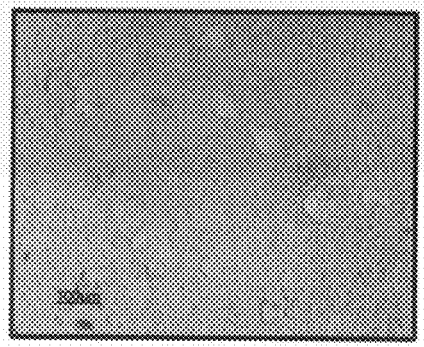
FIG. 4C is a photograph that shows the inhibition effect to pit formation from M-CSF dependent cell from mouse bone marrow cell by honokiol.

As clearly shown in FIG. 4, the pit formation was significantly decreased by the addition of honokiol (10 µM), compared with FIGS. 4A and 4B, which show control wells. The pit is a cavity of the bone resorption formed by the mature osteoclast having the actin rings, and the actin ring is the activated structure of osteoclast formed by culturing of M-CSF dependent cells derived from the mice bone marrow cells treated with M-CSF and TGF-β or ODF/RANKL. Therefore, it was thought that honokiol inhibits not only the differentiation of osteoclast, but also functions of the mature osteoclast, thereby inhibiting the bone resorption.

As a result, it was demonstrated that honokiol and magnolol do not show any non-specific cytotoxicity by itself, when the cell line derived from macrophage or the mice bone marrow cells; they strongly inhibit the differentiation of them to osteoclast induced by RANKL in the dose-dependent manner. Alternatively, honokiol inhibited to maintain the actin ring and to form the pit by the mature osteoclast. It was suggested that honokiol dominantly inhibited the bone resorption by the activated osteoclast.

Example 6

Differentiation Assay of Osteoblast (6-1) Materials and the Like

For the differentiation assay of osteoblast, MC3T3-E1 cells, pre-osteoblast cell line derived from mice (purchased from RIKEN). As a medium for culturing MC3T3-E1 cells, α-MEM including 10% fetal bovine serum was used. The fetal bovine serum and α-MEM were the same as those used in the example 1.

Alternatively, DMSO (dimethylsulfoxide) and MTT (3-(4, 5-Dimethyl-2-thiazolyl)-2,5-diphenyl-2H-tetrazolium Bromide) reagent were purchased from WAKO PURE CHEMICAL Industries Ltd.; p-nitrophenyl phosphate, naphtol AS-MX phosphate, and Fast Blue BB salt were purchased from SIGMA Co. EIA kit for determining the amount of osteocalcin was purchased from Biomedical Technologies Inc.

(6-2) Differentiation Induction Assay

As an evaluation method for the effect against the differentiation of osteoblast, MC3T3-E1 cell osteoblast differentiation induction assay was used. In the assay, the activity of alkaline phosphatase (ALP), the early stage differentiation marker enzyme of osteoblast, was determined, and the staining utilizing the activity (ALP staining) was performed. Expression level of osteocalcin, which is the marker of the differentiated osteoblast, was determined by using the EIA kit described above. Furthermore, in order to know the cytotoxicity, the cell viability was determined by using MTT assay.

(6-2-1) Differentiation Induction of Osteoblast

MC3T3-E1 cells were plated into the wells of the 96-well microplate at the concentration of $4\times10^3$ cells/well, and incubated two days under the presence of 5% of $CO_2$, at 37° C. until cells became confluent in the well.

Figure 5A:
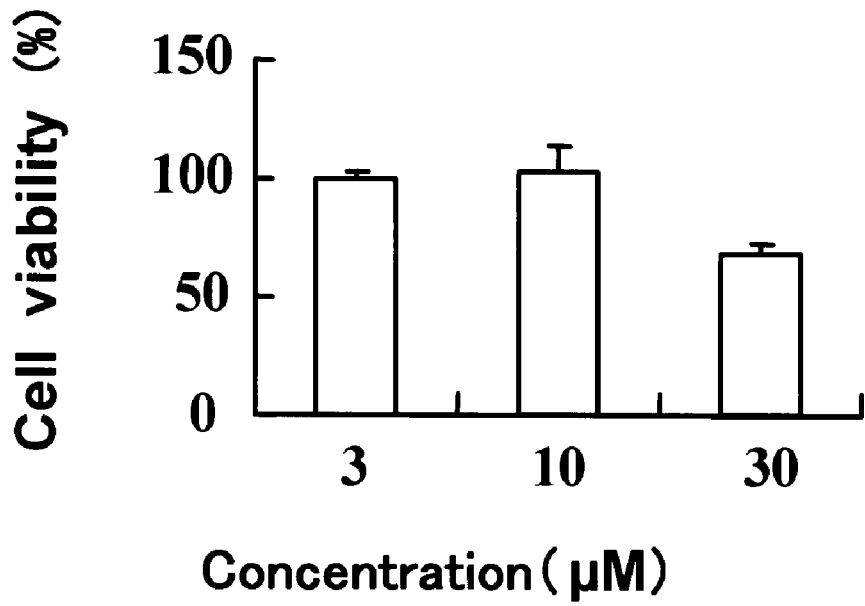
FIG. 5A shows the cell viability of MC3T3-E1 cell by honokiol.
Figure 5B:
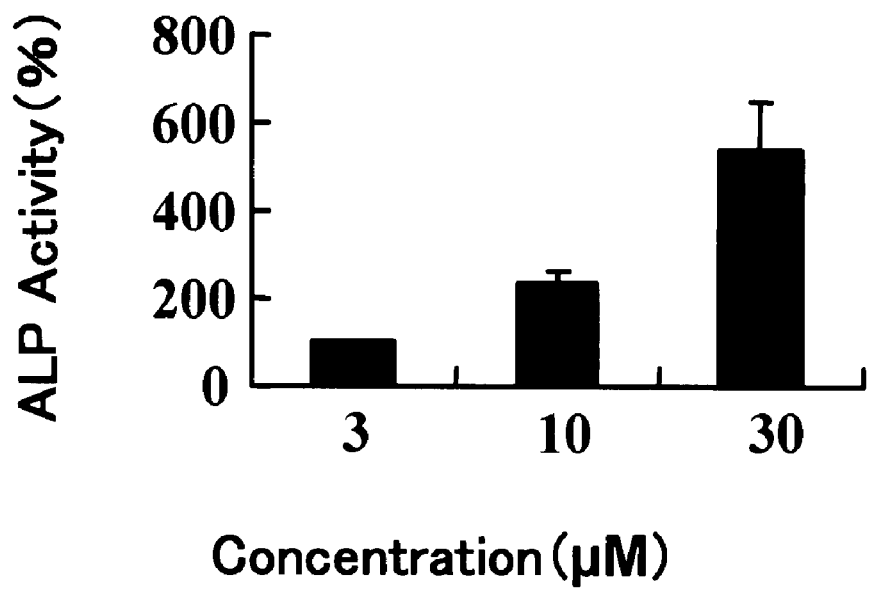
FIG. 5B shows the enhancement of ALP activity of MC3T3-E1 cell by honokiol.
Figure 6:
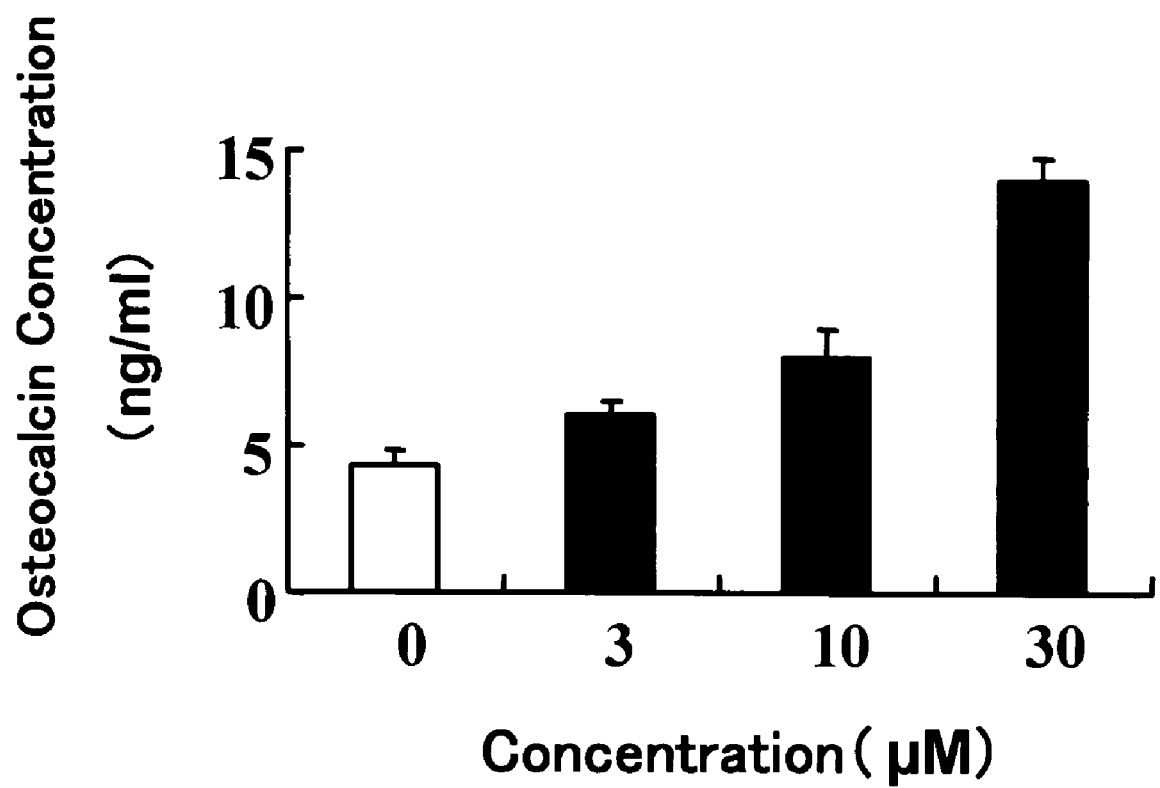
FIG. 6 shows the enhancement of osteocalcin production of MC3T3-E1 by honokiol.

Subsequently, in order to induce the differentiation of osteoblast, they were incubated in α-MEM including 3 to 30 μM of honokiol to which 50 μg/mL of L-ascorbic acid and 10 mM β-glycerophosphate were supplemented, for 7 days or 14 days as shown in FIGS. 5 and 6. The medium was exchanged every 3 or 4 days.

(6-2-2) Bioavailability of the Cells after the Osteoblast Differentiation Induction In order to determine the cell viability, MC3T3-E1 cells were cultured for 7 days under the condition as described above. After that, MTT reagent was added into the well at the 1/10 volume of the medium in the well, and reacted for 1 hour at 37° C. Then, the medium was removed, and generated formazan was dissolved in DMSO; then its absorbance was measured by using microplate reader at the wave length of 570 nm (reference wave length was 630 nm).

Based on the measured absorbance value, the cell viability was obtained as ratio (%) to control wells, when the cell viability in control wells was 100. Results were shown in FIG. 5A.

(6-2-3) Evaluation of Osteoblast Differentiation Induction (1) Determination of ALP Activity ALP activity was determined as follows. At first, MC3T3-E1 cells were cultured for 7 days under the same condition as described above; then the medium was removed, and washed by using PBS. After that cells were fixed by using methanol and the dish was dried.

Then, 100 μL of 100 mM tris-HCl buffer (pH 8.5) including 6.7 mM p-nitrophenylphosphate as a substrate and 2 mM magnesium chloride is added into each well, and reacted for 30 minutes at 37° C.

The reaction was terminated by adding 100 μL of 0.1 N NaOH, and released p-nitrophenol was determined by measuring absorbance at the wave length of 405 nm, by using the plate reader for obtaining ALP activity.

Results of the osteoblast differentiation assay were shown as the ratio (%) to control wells, when the ALP activity of the cells in the control wells was 100. Obtained results were shown in FIG. 5.

(2) ALP Staining

In order to perform ALP staining, a buffer containing 0.1 mg/mL naphtol AS-MX phosphate, 0.6 mg/mL Fast blue BB salt, 2 mM magnesium chloride, and 100 mM tris-HCl (pH 8.5) was used as a staining solution.

After ALP activity was determined as described above, each well was washed by using distilled water, and then 100 μL of the staining solution was added into each well. Subsequently, the reaction was performed at room temperature for 30 minutes to 1 hr.

As shown in FIG. 5A, the cell viability of MC3T3-E1 cells was slightly decreased, when the amount of honokiol added reached 30 μM. In contrast, as clearly shown in FIG. 5B, ALP activity was enhanced in dose dependent manner by the addition of honokiol. Accordingly, it was demonstrated that honokiol slightly inhibited the growth of MC3T3-E1 cells, but it strongly induced the early stage of osteoblast differentiation.

(3) Concentration of Osteocalcin

In order to determine the concentration of osteocalcin, culture supernatant of MC3T3-E1 cells cultured for 14 days under the above-mentioned conditions was used. Amount of osteocalcin in the culture supernatant was determined according to the procedure written on an instruction manual attached to the EIA kit.

As shown in FIG. 6, it was shown that the expression level of osteocalcin was enhanced by adding honokiol in dose dependent manner. As a result, it was demonstrated that honokiol promoted the differentiation of MC3T3-E1 cells to osteoblast.

Accordingly, honokiol and magnolol, which are phenylpropanoid dimmer conventionally used as the crude drug, were useful for the food with health-promoting benefits, pharmaceutical compositions and pharmaceutical preparations for prophylaxis and/or treatment of the bone diseases.

Pharmaceutical Preparation Example

Next, pharmaceutical preparations comprising the composition of the present invention is explained. However, the present invention is not limited to them.

Pharmaceutical Preparation Example 1 Tablet Preparations

TABLE 1

| Component | Amounts (g) |
| --- | --- |
| Honokiol or magnolol | 100 |
| Mannitol | 123 |
| Starch | 33 |
| Povidone (Cross Povidone) | 12 |
| Microcrystalline cellulose | 30 |
| Magnesium stearate | 2 |

The above-mentioned components were weighed respectively, and mixed homogenously. Then, the mixture was compressed to prepare tablets of 300 mg weight for tablet preparations.

Pharmaceutical Preparation 2 Hard Gelatin Capsule Preparations

TABLE 2

| Components | Amounts (g) |
| --- | --- |
| Composition 1 | 40 |
| Lactose | 150 |
| Starch | 70 |
| Polyvinylpyrrolidone | 5 |
| Crystalline cellulose | 35 |

The above-mentioned components were weighed respectively, and mixed homogenously. Then each hard gelatin capsule was filled by 300 mg of the mixture to prepare hard gelatin capsule preparations. Herein, the composition 1 was a mixture of honokiol and lactose at the ration of 1:1. Note that the composition 1 is used in the following Pharmaceutical Preparations 3 to 6.

Pharmaceutical Preparation 3 Soft Elastic Capsule Preparations

TABLE 3

| Components | Amounts (g) |
| --- | --- |
| Composition 1 | 100 |
| Tocopherol | 0.2 |

The above-mentioned components were weighed respectively, and mixed homogenously. Then each soft elastic capsule was filled by 100 mg of the mixture to prepare soft elastic capsule preparations.

Pharmaceutical Preparation Example 5 Granule Preparations

TABLE 4

| Components | Amounts (g) |
| --- | --- |
| Composition 1 | 200 |
| Lactose | 450 |
| Corn starch | 300 |
| Hydroxypropyl cellulose | 50 |
| Crystalline cellulose | 35 |

Components of the above-mentioned were weighed as the amounts described above, and mixed homogenously. Then, granule preparations are prepared according to conventional procedure.

Pharmaceutical Preparation Example 5 Syrup Preparations

TABLE 5

| Components | Amounts (g) |
| --- | --- |
| Composition 1 | 2 |
| Saccharin | 0.6 |
| Glucose | 30 |
| Glycerin | 5 |
| Seasoning agent | 0.1 |
| 96% ethanol | 10.4 |
| Distilled water | necessary amount to adjust to final amount as 100 mL |

Components of the above-mentioned were weighed as the amounts described above. Glucose and saccharin were dissolved in 60 mL of distilled water for injection, and then the composition 2 dissolved in glycerin and ethanol and seasoning agent were added into the distilled water. Subsequently, distilled water is added into the solution to adjust the volume to 100 mL at final volume to prepare syrup for p.o.

Pharmaceutical Preparation Example 6 Granule Preparations

TABLE 6

| Components | Amounts (g) |
| --- | --- |
| Composition 1 | 100 |
| calcium silicate | 100 |

Components of the above-mentioned were weighed as the amounts described above to produce the composition 3 according to the conventional procedure, and then the composition 3 was adsorbed to calcium silicate to small particle to prepare powder.

INDUSTRIAL APPLICABILITY

The present invention is useful in the field for the pharmaceutical compositions, the pharmaceutical preparations thereof as an active ingredient, the health food, the food with health-promoting benefits and the like.

The invention claimed is:
1. A health food, comprising:
a food; and
at least one compound of formula (I)

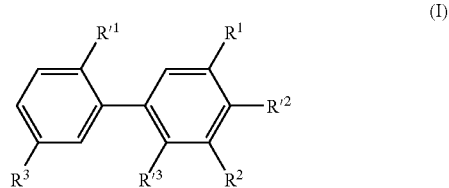

wherein, respective $R'^1$, $R'^2$, and $R'^3$ are independently hydrogen atom, hydroxyl group, or alkoxy group of C1 to C3, and $R^1$, $R^2$, and $R^3$ are hydrogen atom or alkenyl group of C3 to C5, a physiologically acceptable salt thereof, or physiologically acceptable hydrate thereof;
wherein the health food is selected from the group consisting of a cookie, a biscuit, a barley or coarse cereal as an additive for a rice diet, a noodle, dairy product, jam, mayonnaise, a processed soy product, a rice cracker, and a confectionery made of beans.

2. The health food of claim 1, wherein the health food comprises an extract from tree bark of trunks or branches of arbor tree belonging to *Magnolia* genus.

3. The health food according to claim 2, wherein said arbor tree to *Magnolia* genus is selected from the group consisting of *Magnolia officinalis*, *Magnolia officinalis* var, *biloba*, *Magnolia hypoleuca*, *Magnolia macrophylla*, *Magnolia obovata*, *Magnolia salicifolia*, *Magnolia stellata*, *Magnolia salicifolia*, *Magnolia virginiana*, *delavayi*, *Magnolia kobus*, *sieboldii*, and *Magnolia wiilsonii*.

4. The health food of claim 1, wherein the compound of formula (I) is present in the amount of 0.1 to 5 mg per 100 g of the health food.

5. The health food of claim 1, wherein the compound of formula (I) is a compound of formula (II) or (III)

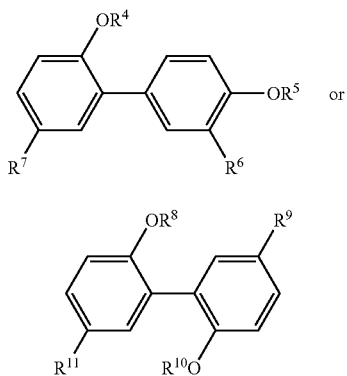

wherein, in formula (II), respective $R^4$, $R^5$, $R^8$ and $R^{10}$ are selected from the group consisting of hydrogen atom, and alkyl group consisting of C1 to C3, and in formula (III), $R^6$, $R^7$, $R^9$, and $R^{11}$ are alkenyl of C3 to C5.

6. The health food of claim 1, wherein the compound of formula (I) is a compound of formula (IV) or (V)

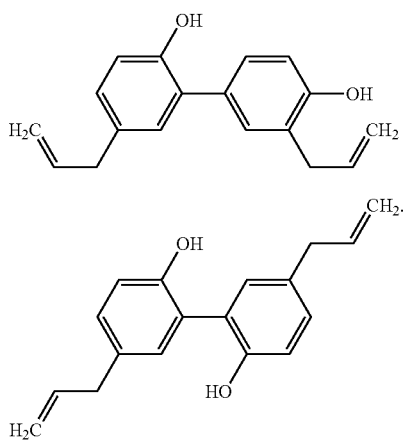

7. The health food of claim 6, comprising both the compound of formula (IV) and the compound of formula (V) in a ratio in the range of 1:0.1 to 1:10, respectively.

8. A pharmaceutical preparation, comprising:
at least one compound of formula (I)

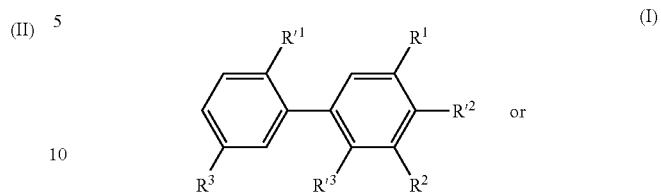

wherein, respective $R'^1$, $R'^2$, and $R'^3$ are independently hydrogen atom, hydroxyl group, or alkoxy group of C1 to C3, and $R^1$, $R^2$, and $R^3$ are hydrogen atom or alkenyl group of C3 to C5, a physiologically acceptable salt thereof, or physiologically acceptable hydrate thereof;
wherein the pharmaceutical preparation is in the form of an injectable, suppository, aerosol, percutaneous, tablet, powder, capsule, pill, troche or liquid.

9. The pharmaceutical preparation of claim 8, wherein the compound of formula (I) is honokiol or magnolol, and the amount of the honokiol or magnolol in a single dosage unit is in the range from 0.1 to 100 mg.

10. A therapeutic method, comprising the step of:
administering to a patient having a bone disease parenterally or per os, at a dosage of 1 mg to 2000 mg/kg, at least one compound of formula (I)

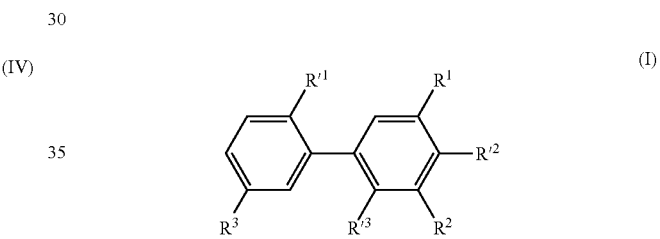

wherein, respective $R'^1$, $R'^2$, and $R'^3$ are independently hydrogen atom, hydroxyl group, or alkoxy group of C1 to C3, and $R^1$, $R^2$, and $R^3$ are hydrogen atom or alkenyl group of C3 to C5, a physiologically acceptable salt thereof, or physiologically acceptable hydrate thereof.

11. A therapeutic method of claim 10, wherein the bone disease is selected from the group consisting of traumatic bone fracture, stress fracture, pre-osteoporosis disease, osteoporosis, hypercalcemia, hyperparathormone disease, Paget's disease, arthritis, rheumatism, metastasis of breast cancer, osteomalacia, malignant neoplasm, and nutritional deficiency.

* * * * *